United States Patent
Kammermeier et al.

(10) Patent No.: US 8,206,622 B2
(45) Date of Patent: Jun. 26, 2012

(54) PROCESS FOR PRODUCTION OF IONICALLY CROSSLINKED POLYSACCHARIDE MICROSPHERES

(75) Inventors: Stefan Kammermeier, Groebenzell (DE); Till Merkel, Neu-Ulm (DE); Katharina Schmid, Aschaffenburg (DE); Achim Müller, Grossostheim (DE)

(73) Assignee: EyeSense AG, Basel (CH)

( * ) Notice: Subject to any disclaimer, the term of this patent is extended or adjusted under 35 U.S.C. 154(b) by 792 days.

(21) Appl. No.: 10/590,316

(22) PCT Filed: Feb. 22, 2005

(86) PCT No.: PCT/EP2005/001850
§ 371 (c)(1),
(2), (4) Date: Nov. 28, 2006

(87) PCT Pub. No.: WO2005/079970
PCT Pub. Date: Sep. 1, 2005

(65) Prior Publication Data
US 2007/0178162 A1    Aug. 2, 2007

(30) Foreign Application Priority Data
Feb. 23, 2004    (EP) .................................... 04003989

(51) Int. Cl.
*B29B 9/00* (2006.01)
(52) U.S. Cl. ................. 264/5; 264/12; 264/13
(58) Field of Classification Search .......... 264/5, 12–13
See application file for complete search history.

(56) References Cited

U.S. PATENT DOCUMENTS

| | | | |
|---|---|---|---|
| 4,352,883 A | * | 10/1982 | Lim .............................. 435/178 |
| 5,387,522 A | | 2/1995 | Vasington et al. |
| 6,465,226 B1 | | 10/2002 | Zimmermann |

FOREIGN PATENT DOCUMENTS

| | | |
|---|---|---|
| EP | 0 167 690 A2 | 1/1986 |
| EP | 0 480 729 B1 | 4/1992 |
| EP | 1 382 341 A1 | 1/2004 |
| EP | 1 502 645 A1 | 2/2005 |
| WO | WO 02/13786 A2 | 2/2002 |
| WO | WO 03/091315 A1 | 11/2003 |

OTHER PUBLICATIONS

Olav Smidsrød et al., "Chemistry and physical properties of alginates", Carbohydrates in Europe 1996, 14, pp. 6-13.

(Continued)

*Primary Examiner* — Christina Johnson
*Assistant Examiner* — Xue Liu
(74) *Attorney, Agent, or Firm* — Fanelli Haag & Kilger PLLC

(57) ABSTRACT

The invention relates to a process for preparing microspheres comprising an ionically crosslinked polymer, the process comprising: (a) producing liquid aerosol droplets (13) from a solution (3) comprising an ionically crosslinkable polyionic polymer into a continuous gas stream by using an ultrasonic nebulizer; (b) transferring the gas stream into a gelling solution (10) comprising di-, multi- or polyvalent ions, whereby crosslinked polymer microspheres (14) are formed, (c) separating the microspheres from the gelling solution, and (d) optionally, filtering the microspheres through a screen.

62 Claims, 3 Drawing Sheets

OTHER PUBLICATIONS

Osato Miyawaki et al., "Permeability and Molecular Sieving Characteristics of Nylon Microcapsule Membrane", Agric. Biol. Chem., 44 (12), 1980, pp. 2865-2870.

Anne C. Hulst et al., "Immobilised Plant Cells: Respiration and Oxygen Transfer", J. Chem. Tech. Biotechnol., 35B, 1985, pp. 198-204.

D.T. O'Hagan, "The intestinal uptake of particles and the implications for drug and antigen delivery", J. Anat. 198, 1996, pp. 477-482.

D. Poncelet et al., "Production of alginate beads by emulsification/internal gelation. II. Physicochemistry", Appl. Microbiol. Biotechnol., 43, 1995, pp. 644-650.

D. Lemoine et al., "Preparation and characterization of alginate microspheres containing a model antigen", International Journal of Pharmaceutics 176, 1998, pp. 9-19.

H. Huang et al., "Preparation and structure of silicon doped tin oxide composites using an advanced ultrasonic spray method", Solid State Ionics 120, 1999, pp. 205-210.

B. Bittner et al., "Ultrasonic atomization for spray drying: a versatile technique for the preparation of protein loaded biodegradable microspheres", J. Microencapsulation, vol. 16, No. 3, 1999, pp. 325-341.

* cited by examiner

PROCESS FOR PRODUCTION OF IONICALLY CROSSLINKED POLYSACCHARIDE MICROSPHERES

The present invention relates to a process for the production of microspheres comprising an ionically crosslinkable polymer and to a system for carrying out the process.

SUMMARY

In this application the term ionically crosslinkable polymer refers to a soluble polyionic polymer that is capable to instantaneously form a sparingly or insoluble gel on contact with a gelling solution comprising divalent, multivalent or polyvalent ions having charges opposite to those of the ionically crosslinkable polymer.

Polyionic polymers that may be employed in the present application comprise polyanionic and polycationic polymers of natural or synthetic origin.

In a first embodiment the polyionic polymers are natural or synthetic polyanions which can be crosslinked by di-, multi- or polyvalent cations. Natural polyanions are e.g. polysaccharides comprising carboxylic acid or sulfate groups (e.g alginic acid, some forms of carrageenan, gellan gum, pectins, cellulose sulphate, and dextran sulphate). Synthetic polyanions are e.g. poly (meth)acrylic acid, polystyrene sulfonate and copolymers thereof, or polymers of the group of polyphosphazenes.

In a further embodiment, the crosslinkable polymer is a natural or synthetic polycation which can be crosslinked by multi- or polyvalent anions. Natural polycations are e.g. amino functionalized polysaccharides like chitosan, aminodextran, or polypeptides like protamine. Synthetic polycations are e.g. poly (allylamine hydrochloride), poly(ethylen imine), poly (diallyldimethylammonium chloride) and polyamide-polyamine-epichlorhydrine.

A particularly preferred group of ionically crosslinkable polyanionic polymers are anionic polysaccharides which are copolymers of monosaccharides comprising a carboxylic acid group, herein referred to as "anionic polysaccharides". Anionic polysaccharides have found widespread application in formulation techniques. A particularly useful characteristic of many anionic polysaccharides is their ability to be readily soluble as free acids and/or salts of monovalent cations while forming strong gels on contact with divalent or polyvalent cations. Within the present application, anionic polysaccharides which instantaneously form gels by reaction with divalent or polyvalent cations, are called "ionically crosslinkable anionic polysaccharides".

Alginic acid is a naturally occurring unbranched binary copolymer of guluronic acid (G) and its C-5 epimer mannuronic acid (M). It has been found that the G- and M-units are joined together in a blockwise fashion. The salts of alginic acids are generally named alginates. Alginates are extracted in large amounts from brown seaweed. The proportions of G and M in the polymer, and the distribution of G and M blocks in the polymer, depends on the source of the alginate (Cf. Carbohydrates in Europe 1996, 14, 6-31).

In most applications alginate gel formation is achieved with calcium ions. However, alginate form gels with most di- and multivalent cations. Monovalent cations and $Mg^{2+}$ ions do not induce gelation while ions like $Ba^{2+}$ and $Sr^{2+}$ will produce stronger alginate gels than $Ca^{2+}$. The gel strength is dependent upon the guluronic acid content and also on the average number of G-units in the G-blocks.

Crosslinked alginates are used, for example, as rheology control additives, as wound dressings or for immobilizing materials such as plant cells, mammalian cells, yeasts, bacteria, vaccines or food products. Alginate gel formation is achieved with calcium ions in most applications.

A number of different methods for the immobilization of biomaterials in alginate beads have been developed. A commonly used way to form alginate gel beads is by adding an alginate solution dropwise to a solution of gelling ions, for example calcium chloride. The droplet size will determine the size of the spheres. A syringe needle has been used for the formation of alginate droplets. However, reduction in bead size is limited by the syringe needle diameter and the viscosity of the solution. As a result, beads with a diameter of less than 1 mm are difficult to produce. Reduction in bead size has been attempted by air jets impinging on the needle (Miyawaki et al., Agric. Biol. Chem. 1980, 44, 2865), electrostatic pulses (EP 0 167 690 B1) or vibrating needles (Hulst et al., J. Chem. Technol. Biotechnol. 1985, 35B, 198).

There is a demand for microspheres with a mean diameter of about 10 μm, since stable non-sedimenting suspensions may be prepared comprising microspheres of this size, and because microspheres having a diameter of 10 μm or less may be taken up by cells allowing a more efficient drug release inside cells (D. T. O'Hagan, J. Anat. 189, 1996, 477-482).

Fine droplets of an alginate solution may be generated by using a spray head, as disclosed, for example, in U.S. Pat. No. 5,387,522 and U.S. Pat. No. 6,465,226. Alginate particles having a diameter of about 200 μm to about 300 μm have been obtained by the above method.

Ca-alginate microspheres may also be obtained by using emulsification methods. Ponceiet, et al., Appl. Microbiol. Biotechnol 1995, 43, 644 have described the production of alginate microspheres by emulsification/internal gelation of alginate sol dispersed within vegetable oil. Gelation was initiated within the alginate sol by reduction in pH releasing calcium from an insoluble complex. Alginate microspheres with mean diameters ranging from 50 μm to 1000 μm were obtained.

Even finer alginate microspheres having a diameter of about 10 μm have been obtained by further optimizing the effects of various operational and formulation factors in the emulsification technique (D. Lemoine, et al., International Journal of Pharmaceutics 1998, 176, 9).

Emulsification techniques for the generation of alginate microspheres are using oils and/or organic solvents. Sensitive biomolecules (proteins, enzymes) may be incompatible with oils and/or organic solvents. Removal of oils and/or organic solvents from alginate microspheres is a tedious and incomplete process.

Therefore, there is a need for a process for the manufacture of microspheres made from a crosslinkable anionic polysaccharide having a size of about 3-20 μm and being devoid of traces of oils and/or organic solvents.

Surprisingly, it has been found that microspheres of crosslinked anionic polysaccharides having a diameter of about 3 to 20 μm which are completely free of oils and/or organic solvents may be obtained by generating fine liquid aerosol droplets from a solution of a water soluble anionic polysaccharide into a stream of a gas and subsequently introducing the stream of gas comprising these droplets into a gelling solution comprising gel-forming cations.

Therefore, in one aspect, the invention relates to a process for preparing microspheres comprising an ionically crosslinked polymer, the process comprising:

(a) producing liquid aerosol droplets (13) from a solution (3) comprising an ionically crosslinkable polyionic polymer into a continuous gas stream by using an ultrasonic nebulizer;

(b) transferring the gas stream into a gelling solution (10) comprising di-, multi- or polyvalent ions, whereby crosslinked polymer microspheres (14) are formed,
(c) separating the microspheres from the gelling solution, and
(d) optionally, filtering the microspheres through a screen.

In another aspect, the invention relates to a system for preparing microspheres comprising an ionically crosslinked polymer, the system comprising
(a) an ultra sound generator (1) situated in a nebulizing chamber (2) which is filled with a solution (3) comprising an ionically crosslinkable polymer;
(b) a radiator coil (4) attached to the nebulizing chamber;
(c) optionally, means (6) for keeping the gas-fluid level (5) in the nebulizing chamber (2) at a predetermined constant level;
(d) a gas inlet (7) attached to the nebulizing chamber (2)
(e) a vessel for the gelling solution (9), equipped with agitation means (11); and
(f) a transfer tubing (8) attached to the nebulizing chamber, connecting nebulizing chamber and vessel, wherein the tubing is adapted to submerge into the gelling solution (10).

The agitation means (11) are selected from tools which are known from the formation of dispersions or emulsions. Preferred agitation means is ultrasound.

SHORT DESCRIPTION OF THE DRAWINGS

DETAILED DESCRIPTION

Key part of the system is an ultrasonic nebulizer. A device as being used in air conditioning systems for air moistening may be used. A suitable nebulizer is, for example, the air moistening device SCA 1000, manufactured by Stulz GmbH, D-22457 Hamburg.

Preferably, the radiator coil (4) is connected to means for keeping the temperature of the solution to be nebulized at a predetermined range.

Preferred temperature ranges of the solution to be nebulized are of from 15 to 50° C., in particular of from 25 to 35° C.

It is preferred to dip the tubing connecting nebulizing chamber (2) and vessel (9) as deep as possible into the bath of the gelling solution (10) to allow the aerosol droplets (13) comprising crosslinkable polymer to interact with the di-, multi- or polyvalent counterions of the gelling solution to form crosslinked microspheres (14).

It is further preferred that the lower part of the tubing which submerges into the gelling solution comprises dispenser holes (12).

As mentioned above, the process of the invention may be carried out with different ionically crosslinkable polymers.

Preferred crosslinkable natural polyanions are selected from the group consisting of an alginic acid, a carrageenan, a cellulose sulphate, a dextran sulphate, a gellan, a pectin and water soluble salts thereof. Most preferred anionic polysaccharide is alginic acid or a water soluble salt thereof.

Particularly preferred crosslinkable natural polyanions are $Na^+$-, $K^+$-, $NH_4^+$-, and $Mg^{2+}$-salts of alginic acid and $Na^+$-, $K^+$-, and $NH_4^+$-salts of gellan, carrageenan and cellulose sulphate.

Preferably, the liquid to be nebulized (3) comprises the crosslinkable natural polyanion in a concentration of from 0.1% to 5.0% by weight, particularly of from 0.75% to 1.5% by weight.

A particularly preferred liquid to be nebulized comprises of from 0.75% to 1.5% by weight low viscosity sodium alginate.

Preferred crosslinkable synthetic polyanions are selected from the group consisting of linear or branched polyacrylic acid, poly (meth)acrylic acid, polystyrene sulfonate, polyanions of the group of polyphosphazenes, and copolymers and water soluble salts thereof.

Preferred crosslinkable natural polycations are selected from the group consisting of amino functionalized polysaccharides like chitosan, amino-dextran, polypeptides like protamine and water soluble salts thereof.

Preferred crosslinkable synthetic polycations are selected from the group consisting of poly allylamine, poly(ethylen imine), poly (diallyidimethylammonium chloride), polyamide-polyamine-epichlorhydrine, (amino-)dextrans, polypeptides and water soluble salts thereof.

The stream of gas may be generated by pressurized air. However, other gases, in particular inert gases, for example nitrogen or argon, are also well suited. The gas should be purified before usage.

The gelling solution comprises a salt of a gel-forming di- or multivalent cation or anion, polyvalent cation or anion, e.g. water soluble salts of polycations or polyanions, depending on the nature of the crosslinkable polymer.

The gelling solution for natural or synthetic polyanions comprises a salt of a gel-forming di-, multi- or polyvalent cation in a concentration of from 0.1% by weight up to saturated solutions.

Preferred concentrations of the salt comprising a gel-forming di- or multivalent cation are 0.5 to 5% by weight. Gel-forming di- or multivalent cations are, for example, $Pb^{2+}$, $Be^{2+}$, $Ca^{2+}$, $Ba^{2+}$, $Sr^{2+}$ $Zn^{2+}$, $Cu^{2+}$, $Mn^{2+}$, $Co^{2+}$, $Fe^{2+}$, $Fe^{3+}$, $Al^{3+}$ and $Sn^{4+}$.

In the case of the formation of alginate microspheres by the present process, it is preferred to apply a gel-forming cation selected from the group consisting of $Ba^{2+}$, $Sr^{2+}$, and $Ca^{2+}$. Most preferred cation for crosslinking alginate is $Ca^{2+}$.

Gel-forming polyvalent cations are, for example, poly(allylamine hydrochloride), poly(ethylene imine), poly(diallyidimethylammonium chloride), polyamide-polyamine-epichlorhydrine, chitosan, amino-dextran, and protamine sulfate.

The gelling solution for natural or synthetic polycations comprises a salt of a gel-forming multi- or polyvalent anion in a concentration of from 0.1% by weight up to saturated solutions.

Gel-forming multivalent anions are, for example, phosphate, sulfate, citrate, oxalate, borate. Gel-forming polyvalent anions are, e.g., poly (meth)acrylic acid, polystyrene sulfonate, dextran sulfate.

It is understood that the gelling solution has to be adapted according to the gelling characteristics of a specific crosslinkable polymer. A person skilled in the art knows how to select suitable divalent or polyvalent cations or anions.

The gelling solution is preferably essentially aqueous, but may comprise up to 25% by weight, preferably 0 to 10% by weight of one or more cosolvents. Suitable cosolvents include alcohols, for example, ethanol, isopropanol, glycols, and glycerin; esters, for example, ethyl acetate; or amides, for example, dimethyl formamide.

Preferably, the gelling solution comprises up to 1.0% by weight, in particular of from 0.05 to 0.15% by weight of a surfactant. Suitable surfactants are, for example, polyoxyethylene-sorbitans (e.g., TWEEN®), polyoxyethylated glycol monoethers, or surfactants comprising a block copolymer of ethylene oxide and/or propylene oxide (e.g. poloxamers or poloxamines). A particularly preferred surfactant is poly (oxyethylene)20-sorbitane monolaureate (TWEEN® 20).

The gelling solution may additionally comprise polyelectrolytes which stabilize the crosslinked microspheres by a surface coating.

The alginate microspheres prepared by the method described in the invention are the first microspheres in the low micrometer range which are produced without using an emulsion method. Thus, no oil or non polar organic solvent is needed which might interfere with biomolecules or living cells. Therefore, no subsequent tedious purification steps are required to remove any residual oil or non polar organic solvent.

Small alginate microspheres can be added to solutions (e.g. juice, medicinal drops) without sedimentation. Thus, a homogenous suspension of a drug entrapped in an alginate microsphere can be prepared.

Additionally, as mentioned above, microspheres with a mean diameter below 10 μm can be taken up by a cell which allows a more efficient drug release inside cells.

Furthermore, the size distribution of the microspheres produced by the present process is very narrow and reproducible (generally about 2 to 15 μm, with an average diameter of about 8 μm) compared to other methods described in literature. Preferably, ≧95% of the microspheres produced by the present process have a diameter of from 3 to 20 μm. This narrow size distribution of the alginate microspheres guarantee a more homogeneous loading and release of drugs or biomolecules.

For a controlled drug release it is very important to have a constant release rate to avoid over or under dosing. To achieve this, a tight control of the surface to volume ratio of the microspheres is necessary. The surface to volume ratio is determined by the size distribution. Thus, a narrow size distribution results in a reproducible surface to volume ratio and finally a controlled drug release.

Example

Preparation of Alginate Microspheres

Figure 1:
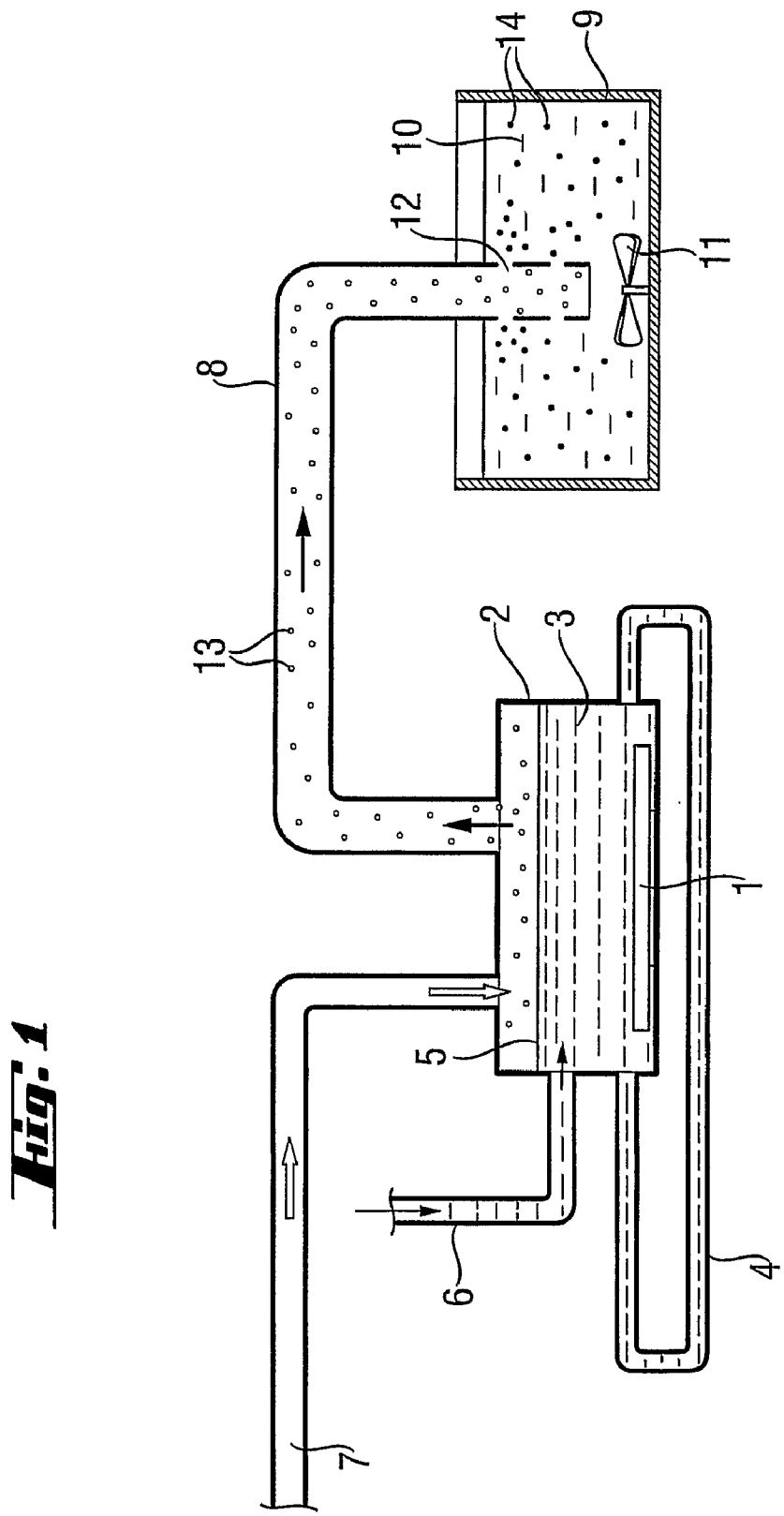
FIG. 1 is a schematic picture of the system for the production of microspheres according to the invention.
Figure 3:
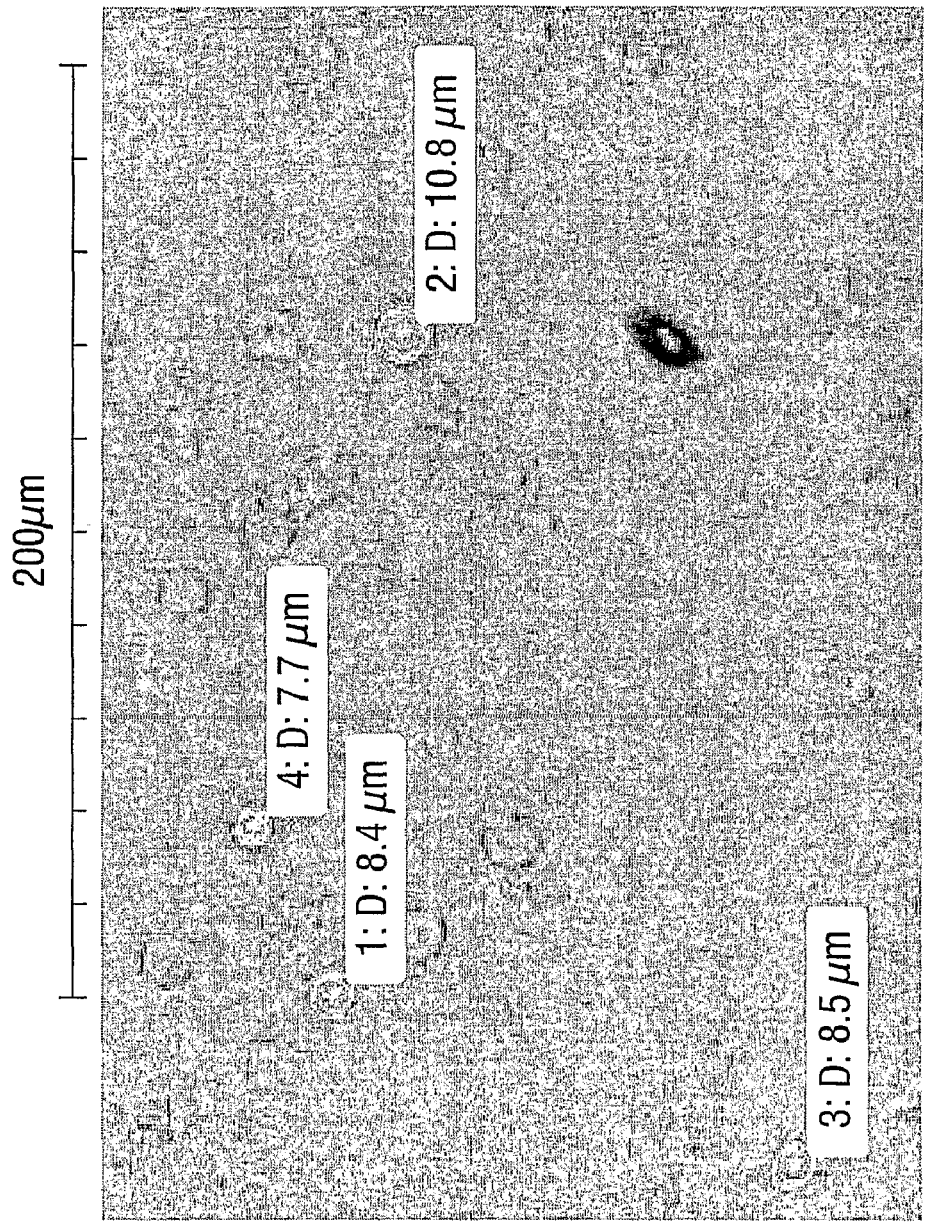
FIG. 3 is a picture of alginate microspheres manufactured according to the process of the invention wherein the diameter of selected microspheres has been determined.

A 1% wt. solution of sodium alginate (Sigma, from brown algae macrocystis pyrifera (kelp), low viscosity) in ultra pure water is filled into the nebulizing chamber (2) of a system according to FIG. 1. The temperature of the radiator coil (4) is adjusted to maintain a temperature of from 25 to 30° C. in the nebulizing chamber. The transfer tubing (8) is dipped into an ultra sound bath (35 kHz) which is filled with 1500 ml of a gelling solution of 5% by weight of $CaCl_2$ and 0.1% by weight of TWEEN 20 (Poly(oxyethylene)20-sorbitane monolaureate) in water. The pressured air is adjusted to produce a slight stream of air bubbles through the $CaCl_2$ bath. Then, the ultra sound generator is turned on for 30 min. The precipitation bath turns turbid which indicates the formation of alginate spheres. To remove very large particles which are generated by condensation of aerosol droplets on the walls of the transfer tube, the alginate—$CaCl_2$ mixture is filtered though a 50 μm screen cloth. The alginate microspheres are separated from the $CaCl_2$ bath by centrifugation (10 min, 1000×g) and decanting of the supernatant. The size of the alginate microspheres was determined to be between 5 and 10 μm by microscopy imaging (see FIG. 3).

Figure 2:
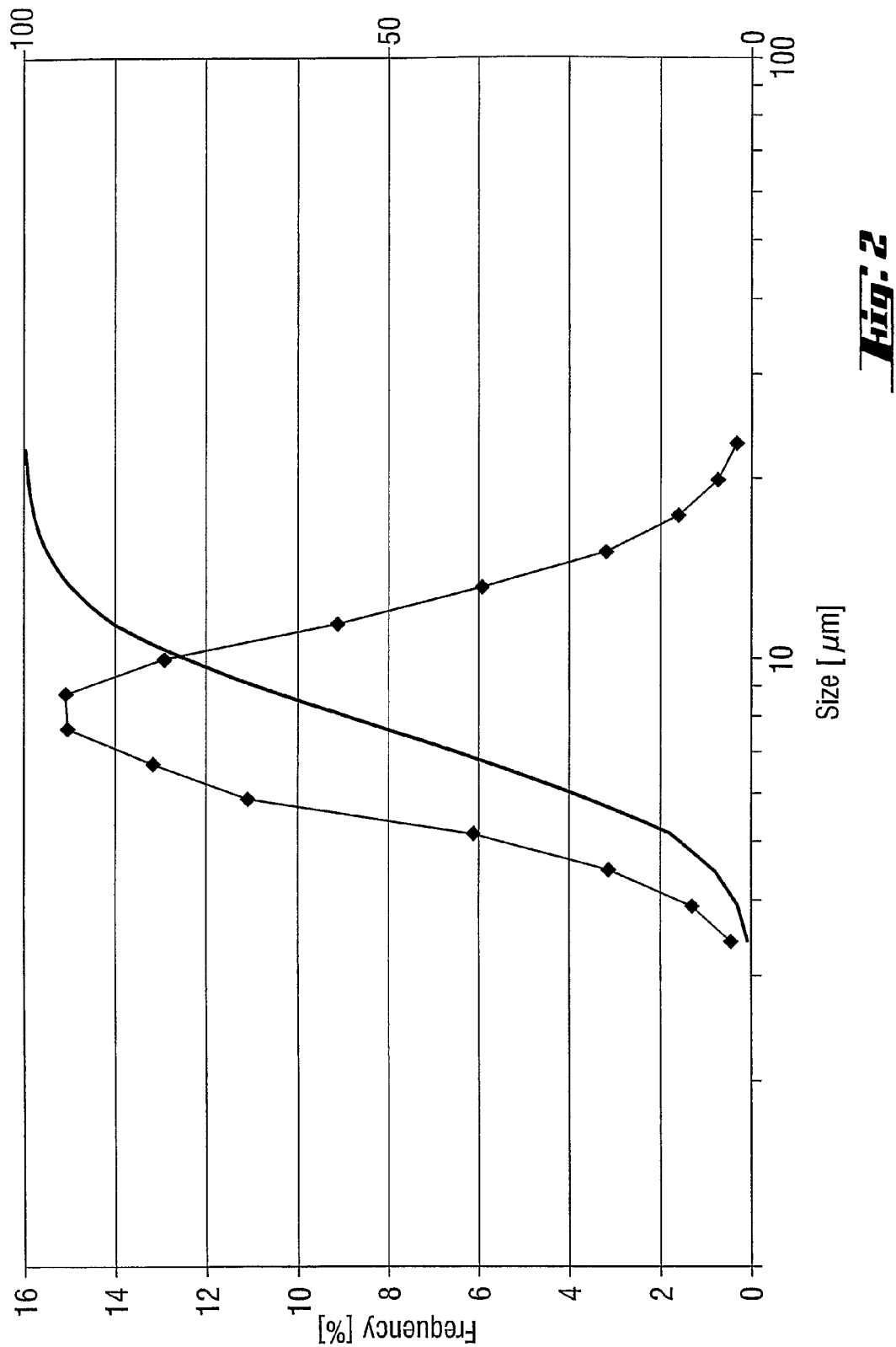
FIG. 2 is a size distribution of alginate microspheres manufactured by the process of the invention.

The size distribution of the alginate microspheres is determined with a laser scattering particle size distribution analyzer (LA-910 from Horiba, Ltd. Kyoto, Japan). A refractive index of 1.35 is used for the alginate microspheres. More than 90% of the spheres are in a range of 5 to 13 μm with the average at 8 μm (FIG. 2).

The invention claimed is:

1. A process for preparing microspheres comprising an ionically crosslinked polymer, the process comprising:
    (a) producing liquid aerosol droplets from a solution comprising an ionically crosslinkable polyionic polymer into a continuous gas stream by using an ultrasonic nebulizer;
    (b) transferring the gas stream into a gelling solution comprising di-, multi- or polyvalent ions, whereby crosslinked polymer microspheres are formed, and
    (c) separating the microspheres from the gelling solution.

2. The process according to claim 1, wherein the ionically crosslinkable polymer is a polyanionic polymer and wherein the gelling solution comprises a polyvalent cation.

3. The process according to claim 2, wherein the polyvalent cation of the gelling solution is selected from the group consisting of poly (allylamine hydrochloride), poly(ethylene imine), poly(diallyldimethylammonium chloride), polyamide-polyamine-epichlorhydrine, chitosan, amino-dextran, and protamine sulfate.

4. The process according to claim 1, wherein the ionically crosslinkable polymer is a polyanionic polymer and wherein the gelling solution comprises di-, multi- or polyvalent cations.

5. The process according to claim 4, wherein the polyanionic polymer is selected from the group consisting of anionic polysaccharides, a linear or branched polyacrylic acid, and polystyrene sulfonate.

6. The process according to claim 5, wherein the anionic polysaccharide is selected from the group consisting of an alginic acid, a carrageenan, a cellulose sulphate, a dextran sulphate, a gellan, a pectin and water soluble salts thereof.

7. The process according to claim 6, wherein the anionic polysaccharide is an alginic acid or a water soluble salt thereof.

8. The process according to claim 4, wherein, in step (a), the polyanionic polymer is present in a concentration of from 0.1% to 5.0% by weight.

9. The process according to claim 4, wherein the ion of the gelling solution is a metal cation selected from the group consisting of $Pb^{2+}$, $Cu^{2+}$, $Ba^{2+}$, $Sr^{2+}$, $Cd^{2+}$, $Ca^{2+}$, $Zn^{2+}$, $Co^{2+}$, and $Ni^{2+}$.

10. The process according to claim 9, wherein the metal cation of the gelling solution is selected from the group consisting of $Ba^{2+}$, $Sr^{2+}$, and $Ca^{2+}$.

11. The process according to claim 10, wherein the metal cation of the gelling solution is $Ca^{2+}$.

12. The process according to claim 1, wherein the gelling solution additionally comprises up to 1% by weight of a surfactant.

13. The process according to claim 12, wherein the surfactant is present in an amount of from 0.02 to 1.0% by weight.

14. The process according to claim 12, wherein the surfactant is selected from the group consisting of polyoxyethylene-sorbitans and surfactants comprising a block copolymer of ethylene oxide and/or propylene oxide.

15. The process according to claim 1, wherein the temperature of the solution of the ionically crosslinkable polyionic polymer according to step (a) is kept within a temperature of from 15 to 50° C.

16. The process according to claim 4, wherein, in step (a), the solution comprises of from 0.75% to 1.5% by weight low viscosity sodium alginate, wherein the cation is Ca2+; and wherein the gelling solution comprises of from 0.05% to 0.15% by weight of poly(oxyethylene)20-sorbitane monolaureate.

17. The process according to claim 1, further comprising:
(d) filtering the micro spheres through a screen.

18. The process according to claim 13, wherein the surfactant is present in an amount of from 0.05 to 0.15% by weight.

19. The process according to claim 15, wherein the temperature of the solution of the ionically crosslinkable polyionic polymer according to step (a) is kept within a temperature of from 25 to 35° C.

20. A process for preparing microspheres comprising an ionically crosslinked polymer, the process comprising:
(a) producing liquid aerosol droplets from a solution comprising an ionically crosslinkable polyionic polymer into a continuous gas stream by using an ultrasonic nebulizer;
(b) submerging the gas stream via a tubing comprising dispenser holes into a gelling solution comprising di-, multi- or polyvalent ions, whereby crosslinked polymer microspheres are formed, and
(c) separating the microspheres from the gelling solution.

21. The process according to claim 20, wherein the ionically crosslinkable polymer is a polyanionic polymer and wherein the gelling solution comprises a polyvalent cation.

22. The process according to claim 21, wherein the polyvalent cation of the gelling solution is selected from the group consisting of poly (allylamine hydrochloride), poly(ethylene imine), poly(diallyldimethylammonium chloride), polyamide-polyamine-epichlorhydrine, chitosan, amino-dextran, and protamine sulfate.

23. The process according to claim 20, wherein the ionically crosslinkable polymer is a polyanionic polymer and wherein the gelling solution comprises di-, multi- or polyvalent cations.

24. The process according to claim 23, wherein the polyanionic polymer is selected from the group consisting of anionic polysaccharides, a linear or branched polyacrylic acid, and polystyrene sulfonate.

25. The process according to claim 24, wherein the anionic polysaccharide is selected from the group consisting of an alginic acid, a carrageenan, a cellulose sulphate, a dextran sulphate, a gellan, a pectin and water soluble salts thereof.

26. The process according to claim 25, wherein the anionic polysaccharide is an alginic acid or a water soluble salt thereof.

27. The process according to claim 23, wherein, in step (a), the polyanionic polymer is present in a concentration of from 0.1% to 5.0% by weight.

28. The process according to claim 23, wherein the ion of the gelling solution is a metal cation selected from the group consisting of Pb2+, Cu2+, Ba2+, Sr2+, Cd2+, Ca2+, Zn2+, Co2+, and Ni2+.

29. The process according to claim 28, wherein the metal cation of the gelling solution is selected from the group consisting of Ba2+, Sr2+, and Ca2+.

30. The process according to claim 29, wherein the metal cation of the gelling solution is Ca2+.

31. The process according to claim 20, wherein the gelling solution additionally comprises up to 1% by weight of a surfactant.

32. The process according to claim 31, wherein the surfactant is present in an amount of from 0.02 to 1.0% by weight.

33. The process according to claim 31, wherein the surfactant is selected from the group consisting of polyoxyethylene-sorbitans and surfactants comprising a block copolymer of ethylene oxide and/or propylene oxide.

34. The process according to claim 20, wherein the solution of the ionically crosslinkable polyionic polymer according to step (a) is kept within a temperature of from 15 to 50° C.

35. The process according to claim 23, wherein, in step (a), the solution comprises of from 0.75% to 1.5% by weight low viscosity sodium alginate, wherein the cation is Ca2+; and wherein the gelling solution comprises of from 0.05% to 0.15% by weight of poly(oxyethylene)20-sorbitane monolaureate.

36. The process according to claim 20, further comprising:
(d) filtering the micro spheres through a screen.

37. The process according to claim 32, wherein the surfactant is present in an amount of from 0.05 to 0.15% by weight.

38. The process according to claim 34, wherein the solution of the ionically crosslinkable polyionic polymer according to step (a) is kept within a temperature of from 25 to 35° C.

39. A process for preparing microspheres comprising an ionically crosslinked polymer, the process comprising:
(a) producing liquid aerosol droplets from a solution comprising a polyanionic polymer and from 0.75% to 1.5% by weight low viscosity sodium alginate into a continuous gas stream by using an ultrasonic nebulizer;
(b) submerging the gas stream into a gelling solution comprising Ca2+ and from 0.05% to 0.15% by weight of poly(oxyethylene)20-sorbitane monolaureate, whereby crosslinked polymer microspheres are formed, and
(c) separating the microspheres from the gelling solution.

40. The process according to claim 38, wherein the gelling solution additionally comprises up to 1% by weight of a surfactant.

41. The process according to claim 40, wherein the surfactant is present in an amount of from 0.02 to 1.0% by weight.

42. The process according to claim 40, wherein the surfactant is selected from the group consisting of polyoxyethylene-sorbitans and surfactants comprising a block copolymer of ethylene oxide and/or propylene oxide.

43. The process according to claim 39, wherein the solution according to step (a) is kept within a temperature of from 15 to 50° C.

44. The process according to claim 39, further comprising:
(d) filtering the micro spheres through a screen.

45. The process according to claim 40, wherein the surfactant is present in an amount of from 0.05 to 0.15% by weight.

46. The process according to claim 43, wherein the solution according to step (a) is kept within a temperature of from 25 to 35° C.

47. A process for preparing microspheres comprising an ionically crosslinked polymer, the process comprising:
(a) producing liquid aerosol droplets from a solution comprising an ionically crosslinkable polyionic polymer into a continuous gas stream by using an ultrasonic nebulizer, wherein the solution of the ionically crosslinkable polyionic polymer is kept within a temperature of from 15 to 50° C.;
(b) submerging the gas stream into a gelling solution comprising di-, multi- or polyvalent ions, whereby crosslinked polymer microspheres are formed, and
(c) separating the microspheres from the gelling solution.

48. The process according to claim 47, wherein the ionically crosslinkable polymer is a polyanionic polymer and wherein the gelling solution comprises a polyvalent cation.

49. The process according to claim 48, wherein the polyvalent cation of the gelling solution is selected from the group consisting of poly (allylamine hydrochloride), poly(ethylene imine), poly(diallyldimethylammonium chloride), polyamide-polyamine-epichlorhydrine, chitosan, amino-dextran, and protamine sulfate.

50. The process according to claim 47, wherein the ionically crosslinkable polymer is a polyanionic polymer and wherein the gelling solution comprises di-, multi- or polyvalent cations.

51. The process according to claim 50, wherein the polyanionic polymer is selected from the group consisting of anionic polysaccharides, a linear or branched polyacrylic acid, and polystyrene sulfonate.

52. The process according to claim 51, wherein the anionic polysaccharide is selected from the group consisting of an alginic acid, a carrageenan, a cellulose sulphate, a dextran sulphate, a gellan, a pectin and water soluble salts thereof.

53. The process according to claim 52, wherein the anionic polysaccharide is an alginic acid or a water soluble salt thereof.

54. The process according to claim 50, wherein, in step (a), the polyanionic polymer is present in a concentration of from 0.1% to 5.0% by weight.

55. The process according to claim 50, wherein the ion of the gelling solution is a metal cation selected from the group consisting of $Pb^{2+}$, $Cu^{2+}$, $Ba^{2+}$, $Sr^{2+}$, $Cd^{2+}$, $Ca^{2+}$, $Zn^{2+}$, $Co^{2+}$, and $Ni^{2+}$.

56. The process according to claim 55, wherein the metal cation of the gelling solution is selected from the group consisting of $Ba^{2+}$, $Sr^{2+}$, and $Ca^{2+}$.

57. The process according to claim 56, wherein the metal cation of the gelling solution is $Ca^{2+}$.

58. The process according to claim 47, wherein the gelling solution additionally comprises up to 1% by weight of a surfactant.

59. The process according to claim 58, wherein the surfactant is present in an amount of from 0.02 to 1.0% by weight.

60. The process according to claim 58, wherein the surfactant is selected from the group consisting of polyoxyethylene-sorbitans and surfactants comprising a block copolymer of ethylene oxide and/or propylene oxide.

61. The process according to claim 50, wherein, in step (a), the solution comprises of from 0.75% to 1.5% by weight low viscosity sodium alginate, wherein the cation is $Ca^{2+}$; and wherein the gelling solution comprises of from 0.05% to 0.15% by weight of poly(oxyethylene)20-sorbitane monolaureate.

62. The process according to claim 47, wherein the solution according to step (a) is kept within a temperature of from 25 to 35° C.

* * * * *